United States Patent [19]

Papadakis et al.

[11] Patent Number: 4,536,274
[45] Date of Patent: Aug. 20, 1985

[54] PH AND CO₂ SENSING DEVICE AND METHOD OF MAKING THE SAME

[75] Inventors: Nicholas Papadakis, Concord; Daniel G. Kalynchuk, University Heights, both of Ohio

[73] Assignee: Diamond Shamrock Chemicals Company, Dallas, Tex.

[21] Appl. No.: 486,024

[22] Filed: Apr. 18, 1983

[51] Int. Cl.³ .............................. G01N 27/56
[52] U.S. Cl. ................ 204/433; 204/415; 204/418; 204/56 R; 324/438; 427/124; 427/125
[58] Field of Search .......... 204/415, 403, 416, 418, 204/430, 431, 433, 39, 56 R; 128/635; 29/570; 427/123, 124, 125; 324/438

[56] References Cited

U.S. PATENT DOCUMENTS

| | | | |
|---|---|---|---|
| 3,671,414 | 6/1972 | Grubb | 204/433 |
| 3,705,088 | 12/1972 | Niedrach et al. | 204/195 P |
| 3,709,810 | 1/1973 | Grubb et al. | 204/433 X |
| 3,856,649 | 12/1974 | Genshaw et al. | 204/418 |
| 3,905,889 | 9/1975 | Macur et al. | 204/195 M |
| 4,133,735 | 1/1979 | Afromowitz et al. | 204/420 X |
| 4,324,256 | 4/1982 | Vesterager | 128/635 |
| 4,409,980 | 10/1983 | Yano et al. | 128/635 |

FOREIGN PATENT DOCUMENTS

| | | |
|---|---|---|
| 2148260 | 4/1972 | Fed. Rep. of Germany . |
| 2426904 | 1/1980 | France .............. 128/635 |

OTHER PUBLICATIONS

Science, vol. 207, Jan. 11, 1980, pp. 188–189.
Acta Anaesth. Scand. 1978, Suppl. 68, 137–141 "Low Impedance pH Sensitive Electrochemical Devices that are Potentially Applicable to Transcutaneous $P_{CO_2}$ Measurements".
Anal. Chem. 1980, 52, 270–273 "Palladium-Palladium Oxide pH Electrodes".
Acta Anaesth. Scand. 1978, 68 111–117 "An Improved Sensor and a Method for Transcutaneous $CO_2$ Monitoring".

Primary Examiner—G. L. Kaplan
Assistant Examiner—Nam X. Nguyen
Attorney, Agent, or Firm—William A. Skinner; Woodrow W. Ban

[57] ABSTRACT

A transcutaneous blood carbon dioxide sensor together with a method for making such a sensor and for making electrodes used in the sensor. The sensor comprises a palladium/palladium oxide junction type electrode and a silver/silver halide junction type electrode applied to an electrically nonconductive substrate, partially coated with an insulative dielectric and partially coated with a polymeric membrane material including a bound electrolyte, the polymeric membrane material being permeable to carbon dioxide. The Pd/PD0 electrode was made cathodic prior to terminating the electro-oxidizing conditions.

13 Claims, 9 Drawing Figures

PH AND CO₂ SENSING DEVICE AND METHOD OF MAKING THE SAME

FIELD OF THE INVENTION

This invention relates to medical devices and methods for their making and more particularly to medical devices for the continuous or semicontinuous monitoring of factors relevant to the health of animals and humans. More specifically this invention relates to a solid state sensor for the analysis of properties of a biological fluid such as pH, and most particularly this invention relates to such sensors including a bound electrolyte for the transcutaneous sensing of carbon dioxide levels in the bloodstreams of animals and humans.

BACKGROUND OF THE INVENTION

Electrolytic means for detecting and measuring the pH (a measurement of the hydrogen-ion activity of a liquid system) are well known. Generally such pH sensors include a glass membrane type electrode and a reference electrode. These glass electrodes tend to be quite fragile, and are therefore not generally suitable for applications involving a considerable amount of movement or jostling or shock. In addition these glass membrane type electrodes generally manifest an elevated electrical impedance. This elevated electrical impedance can make electrical circuitry necessary for evaluating an electrical signal produced by the glass electrode and providing information as to the pH of a solution in which the glass electrode is immersed, more complicated, and often more expensive.

Other pH sensing electrodes, for example those utilizing a polymeric electroactive material, have been proposed. Such polymeric based electrodes, installed subcutaneously, have been utilized to measure, for example, the pH within a human body. One difficulty with polymeric electrodes generally concerns selectivity, particularly with respect to interference arising from the presence of potassium or sodium ions both present in significant quantity in the human body.

pH electrodes of a junction type comprising a palladium wire and including palladium oxide have been proposed for sensing the pH of solutions and other fluids. In addition to an active or pH electrode, a reference electrode is generally required where measuring pH. A wire-like palladium/palladium oxide junction type pH electrode can complicate the making, positioning and supporting of a suitable reference electrode, particularly where the pH electrode and reference electrodes are being miniaturized. Junction type electrodes include an interface or transition region between an electrical conductor and an electrical semi-conductor.

It has long been known that in fluids and fluid solutions otherwise identical but for differing quantities of dissolved carbon dioxide, the pH of each respective solution may be closely correlated to the carbon dioxide content of the solutions. Therefore, sensing devices having electrodes useful for the determination of a pH, often may find utility in determining the dissolved carbon dioxide content of a particular fluid.

It has been proposed that pH sensors be employed for the non-invasive measurement of blood carbon dioxide in humans and animals. In such blood carbon dioxide sensors, a pH electrode and a reference electrode generally are bundled together, encapsulated in a selectively permeable polymeric membrane. The polymeric membrane generally includes an electrolyte, the membrane being impermeable to the elecrolyte but permeable to carbon dioxide gases. The bundle, including probe, reference probe, and encapsulating membrane are applied to a human or animal skin surface. Carbon dioxide diffusing from the body of the human or animal through its skin surface passes through the selective membrane becoming dissolved in the electrolyte solution. The pH of the electrolyte solution is thereby altered, an alteration reflected in the electrical output from the pH active electrode. As the electrical output of reference electrode typically is not effected by such changes, a measurement of changes in the electrical output between the reference and active electrodes provides an indication of changes in the value of the pH. Such transcutaneous, or across the skin, blood carbon dioxide gas sensors are often referred to as a type of Severinghaus electrodes.

With Severinghaus electrodes, two additional difficulties are often encountered in supplement to those difficulties common to pH glass electrodes. Such Severinghaus electrodes generally require a heating of the human or animal skin to which they are applied to a range of temperature of between 43° C. and 45° C. so as to promote vasodilation of subcutaneous blood vessels adjacent the sensor. Vasodilation promotes blood flow through regions of the skin adjacent the sensor and thereby increases the amount of carbon dioxide available for diffusion through the skin and therefore available for sensing at the Severinghaus electrode. These elevated temperatures may contribute to a burning of the skin to which such a Severinghaus electrode is applied. Particularly, a temperature of 45° C. can often produce a quite significant skin burning effect in a relatively short period of time.

A second problem relates to a requirement that, particularly, glass electrodes comprising a Severinghaus electrode be immersed in electrolyte. Such an immersion of necessity requires that the membrane retain a pool of electrolyte in contact with the Severinghaus electrode. Minor imperfections, defects, or wounds to the membrane can necessitate replacement of the membrane, an exacting procedure often requiring specialized equipment. Following a membrane change-out, generally it is necessary that the resilting rebuilt Severinghaus electrode be recalibrated. Recalibration can also require somewhat specialized equipment and can be time consuming.

Typical electrode heating assemblies are shown in U.S. Pat. No. 4,290,431 (Herber) wherein a semiconducting type heating device is utilized within a transcutaneous oxygen sensor. Similarly, U.S. Pat. No. 4,296,752 (Welsh) provides a heater adjacent the electrode assembly incorporated within the main body of a transcutaneous sensor. These patents, U.S. Pat. No. 4,259,963 (Huch) and British Pat. No. 2,056,689A (Heist) provide examples of a typical membrane configuration.

U.S. Pat. No. 4,276,144 (Hahn) proposes the use of a polymeric gas permeable layer over the end of an electrode in a multi-electrode assembly but fails to show how such materials may be employed in a transcutaneous blood gas sensor assembly. An example of an apparatus for oxygen partial pressure measurement incorporating a transcutaneous blood oxygen sensor is shown, for example, in U.S. Pat. No. 4,269,684 (Zick). Zick, however, suggests a standard type of electrode and liquid electrolyte reservoir.

An extended life, preferably solid state, low electrical impedance, pH sensor including an active electrode and a reference electrode both having an extended service life could find substantial utility in pH measurement functions. Where such a sensor can be encapsulated in a carbon dioxide permeable, electrolyte nonpermeable, polymeric membrane, such a pH sensor offers potential utility for use as a transcutaneous blood carbon dioxide sensor. Particularly where such a blood carbon dioxide gas sensor includes active and reference electrodes that are replaceable without requiring recalibration of such a sensor, its utility, particularly in the field of medical products, is quite promising.

BRIEF DESCRIPTION OF THE INVENTION

The present invention provides a solid state pH sensor. In preferred embodiments the pH sensor of the present invention is configured to perform as a carbon dioxide sensor.

A solid state pH sensor made in accordance with the instant invention includes an electrically nonconductive substrate. Applied to the electrically nonconductive substrate are a metal/metal oxide junction electrode and a separate reference electrode. An insulating dielectric coating is applied over at least portions of the substrate and the electrodes. Optionally, a polymeric membrane is applied over at least those portions of the electrodes not having an applied coating of the insulating dielectric. The polymeric membrane includes a bound liquid electrolyte.

Solid state pH sensors in accordance with the instant invention are made by a process generally begun with the selection of an electrically nonconducting substrate from a group consisting essentially of ceramics, refractories, thermoplastics, and thermosetting resins. A metal is applied to the substrate in a desired physical electrode configuration employing one of thick and thin film techniques. A silver/silver halide junction type reference electrode of a desired physical configuration is also applied to the substrate. Generally the silver is applied first and then in a later step subjected to halogenation conditions. The applied reference electrode and the metal applied in a desired electrode physical configuration together with the substrate are at least partially coated with an insulating dielectric material. The applied metal is then subjected to electro-oxidizing conditions for a period of time necessary to form a desired quantity of an oxide of the metal intermingled with the metal applied to the substrate. The applied metal is made cathodic for at least a brief period prior to terminating the electro-oxidizing conditions. The reference electrode can be applied as silver metal in a desired physical electrode configuration and then treated to form the silver halide either before or after application of the insulating dielectric.

Typically, in preferred methods for making the sensor of the instant invention, the metal is applied by thick film techniques wherein an ink or precursor compound containing the metal is applied to the substrate and then fired to sinter the metal adheringly to the substrate. Once partially oxidized, the applied metal including intermingled metal oxide comprises a junction type active electrode upon the substrate.

Optionally, a polymeric membrane is applied at least to those portions of the electrode and substrate not coated by the insulating dielectric material. The polymeric membrane is one capable of binding a liquid electrolyte within the polymeric membrane. That is to say, the polymeric membrane substantially retains the liquid electrolyte within an infrastructure of the membrane. Where, however, the pH sensor of the instant invention is to be used for purposes of, particularly, transcutaneous carbon dioxide measurements, the polymeric membranes selected for application to the electrodes and substrate should be one readily permeated by carbon dioxide gases.

The above and other features and advantages of the invention will become more apparent when considered in light of the drawings and a detailed description of the invention that follow, together forming a part of the specification.

DESCRIPTION OF THE DRAWINGS

FIG. 5, including

BEST EMBODIMENT OF THE INVENTION

Figure 1:
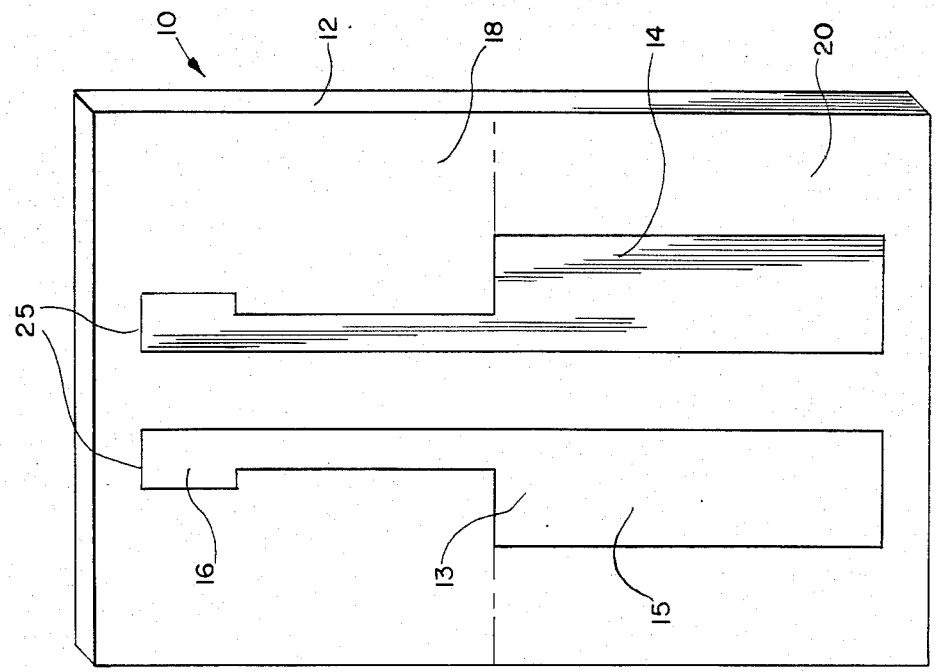
FIG. 1 is a top-view perspective of a pH sensor made in accordance with the instant invention.

Referring to the drawings, FIG. 1 depicts a top perspective view of a pH sensor 10 made in accordance with the instant invention. The pH sensor 10 includes a base 12, an active electrode 13, and a reference electrode 14.

The base or substrate 12 is generally formed from a homogeneous material that is substantially electrically nonconductive. By electrically nonconductive, what is meant is a substance to which the electrodes 13, 14 may be attached, but one which conducts essentially no electrical current away from the electrodes during operation of the sensor. Typically, this substrate is formed from a ceramic, refractory, thermoplastic material, or a thermosetting resin. By ceramic what is meant is a product made by baking or firing of a nonmetallic mineral such as a tile, cement, plaster and brick. By refractory as used herein what is meant is a metal including material or metallic having an elevated melting point. By thermoplastic or thermoplastic resin as used herein what is meant is a material with a linear macromolecular structure capable of repeatedly softening when heated and hardening when cooled. By the term thermosetting resin as used herein what is meant is a plastic material that solidifies when first heated under pressure and which cannot be remelted or remolded without destroying the original characteristics of the resin.

Examples of ceramics would include glasses, as well as tile, cement, plaster and brick. Examples of refractories would include alumina; oxides, borides, nitrides and carbides of; titanium, zirconium, hafnium, vanadium, niobium, tantalum, chromium, molybdenum, tungsten and mixtures thereof. Examples of thermoplastic resins would include styrene, acrylics, cellulosics, polyethylenes, vinyls, nylons and fluorocarbons. Examples of thermosetting resins would include epoxys, furans, malamines, phenolics, and ureas. In this preferred embodiment the substrate 12 is made of a homogeneous alumina material, generally and particularly so called alumina, particles of the homogeneous material being formed or compressed to a desired physical configuration such as one corresponding to the configuration of the substrate or base 12 in FIG. 1. The substrate is then fired to sinteringly coadhere the particles. In equally preferred embodiments, alumina conforming to a desired physical configuration such as that of the substrate 12 may be cut from a larger section of pre-prepared alumina sheet. Cutting of an alumina sheet may be accomplished using a laser or other similar or conventional cutting techniques.

The substrate 12 is physically configured to receive the active electrode 13 and the reference electrode 14 upon one surface of the substrate. Typically for pH sensors in accordance with the instant invention useful in the transcutaneous measurement of blood carbon dioxide levels in animals and humans, the substrate measures approximately 2 centimeters×1 centimeters×250 microns in thickness or thicker. However the particular dimensions are generally not critical and may be of any suitable value.

The active pH electrode 13 is a metal/metal oxide junction type electrode. While the electrode 13 of this best embodiment is shown to be elongated upon the substrate, shape is of no particular importance. The electrode 13 includes a sensing area 15 and an electrical lead contact area 16. The metal comprising the active electrode can be any suitable or conventional electrode conductor having a single stable oxidation state at the particular temperature at which the active electrode is to be operated for pH or $CO_2$ sensing. Preferably this metal is relatively immune to corrosive effects of electrolytes or other substances likely to be encountered by the active electrode while in use. Preferably this metal is selected from a group consisting of palladium, rhodium, ruthenium, osmium, iridium, platinum, tin, antimony, and bismuth. In this preferred embodiment the active electrode metal is palladium.

The active electrode metal is applied to the substrate employing one of thick film techniques, and thin film techniques for metal application or by application of a thin metal section such as a wire or foil. In thin film application techniques the metal is applied directly to the substrate at a temperature promoting coadherence with the substrate. Any suitable or conventional technique for applying a thin film of the metal adheringly to the substrate is satisfactory in the practice of the instant invention provided that the physical dimensions of the electrode metal application can be controlled to be quite nearly equal from one substrate to the next. Plasma spraying or sputtering of the metal onto the substrate is preferred.

In thick film techniques, a compound including the active metal is applied to the substrate, and the applied compound and substrate are then fired to sinter the active metal and to coadhere the active metal substrate. Typically the thick film is applied by silk screening, printing, or the like but equally may be brushed on, sprayed, or the like; and typically the applied compound includes a heat decomposable precursor compound containing the active metal or comprises an ink containing the active metal. Typical inks, or so called metal slurries, are supplied, for example, by Engelhard, E. I. duPont de Nemours, Johnson Matthey, or Cermalloy. Alternately Pd and PdO may be co-mixed with a binder such as an epoxy or furan cement, or polyvinyl alcohol (PVA) and applied to the substrate in suitable or conventional manner. Such electrode would not require later conversion to form PdO.

It is important that the metal in electrode configuration be applied in a thickness and a dimension to the substrate uniform from one substrate to the next so as to forestall the need for recalibrating instrumentation relying upon voltage signals from the sensor for determining a pH or a carbon dioxide content of a substance in contact with the sensor. While a single strip of active metal has been applied to the substrate 12 as shown in FIG. 1, it should be apparent that other configurations such as spirals, interconnected parallel strips, grids, so-called microelectrodes, and the like may be employed.

The active electrode 13 and the substrate 12 are masked in part by an insulating dielectric coating 18 applied in a suitable or conventional manner. Typically this insulating dielectric material is a ceramic electrical insulator. Any suitable or conventional ceramic insulator may be employed, such as ceramic insulation materials supplied by Electroscience Laboratories, Inc. These ceramic insulators frequently are applicable using thick film techniques utilizing a photo-resist and screening process as is well known in the field of thick film fabrication techniques. These ceramic insulators may also be applied using thin film techniques such as, for example, by plasma spraying. The particular method by which these ceramic insulators are applied is not critical to this best embodiment of the invention and the particular application method selected typically is a function of application ease and cost factors.

Prior to application of this ceramic insulator, a reference electrode is adheringly applied to the substrate. The reference electrode is generally a well known junction type metal/metal halide electrode. Typically the reference electrode is a junction type silver/silver halide electrode formed in a suitable or conventional manner such as by applying silver metal to the substrate before application of the dielectric insulation, and then reacting at least a portion of the applied silver metal to produce a silver halide after the dielectric insulation has been applied. While bromides, chlorides and iodides may be employed in producing the junction, a silver/silver chloride reference electrode is preferred in the practice of this invention. Typically the silver reference electrode metal is applied to the substrate using thin or thick film techniques quite similar to those used for applying the active electrode metal.

The active metal electrode is converted to a junction type metal/metal oxide electrode by contacting the applied active metal electrode with an oxidizing environment. Typically one or more of such techniques as electrochemical oxidation, sputtering, plasma deposition, chemical oxidation and air oxidation are employed. In this particularly preferred embodiment, a palladium metal electrode 13 applied to the substrate 12 is anodized in a fused salt electrolyte at approximately 325° C. by making the palladium anodic to a cathode within the fused salt electrolyte. The fused salt electrolyte typically comprises approximately 99.0% (weight) $NaNO_3$ and approximately 1.0% (weight) LiCl. It is believed that other suitable or conventional oxygen imparting fused salt electrolyte baths may be employed for such electrooxidation. Though for anodization, the active electrode adhered to the substrate typically is made anodic while that active electrode is immersed in the fused salt electrolyte, it has been found much preferred that the active electrode be made at least momentarily cathodic prior, and preferably immediately prior to withdrawing the active electrode and substrate from the fused salt electrolyte following the completion of anodization. This cathodic period, however brief, within the fused salt electrolyte performs, it is believed, to stabilize the surface of the active junction type electrode adhered to the substrate and generally provides for superior active electrode performance in pH and $CO_2$ sensing functions.

Typically in an $NaNO_3$-LiCl fused salt electrolyte, the active metal electrode is made anodic at a current of between 0.10 and about 20.0 milliamperes per square centimeters of active metal electrode surface. Preferably the current is between about 2.0 and 5.0 milliamperes per square centimeters. While the active metal electrode is made cathodic within the fused salt electrolyte, the electrical current typically is flowed at between about 2.0 and 5.0 milliamperes per square centimeter of active metal electrode surface area.

Similarly, silver applied for forming a reference electrode is partially halogenated by suitable or conventional chemical or electrochemical techniques for partially halogenating such silver metal where adhered to a substrate. The active electrode and the reference electrode being junction type electrodes, it is important that not all metal comprising either the active or the reference electrode be oxidized/halogenated so as to establish and preserve a junction type electrode performance. Where it is desired that the silver metal be at least partially converted to silver chloride, such a conversion can be accomplished by making the silver metal anodic within an aqueous electrolyte including 1.0 weight percent sodium chloride. The reference electrode is made anodic at 3.5 volts under an extremely low current flow for approximately ten minutes.

The electrodes 13, 14 thus deposited upon the substrate 12, together define an electrical potential between them when contacted with a solution or electrolyte having a particular pH. By measuring an electrical potential difference between the active electrode 13 and the reference electrode 14, as the electrodes together are successively immersed in electrolytes or solutions each of a different pH, a relationship or pattern between a voltage difference between the electrodes 13, 14 and the pH of a particular electrolyte in contact with the electrodes may be established.

Where the application of metals comprising the active electrode and the reference electrode has been closely controlled to assure that electrodes deposited on a plurality of individual substrates are essentially equal in physical dimension and metal content, where such electrodes are successively immersed in identical solutions of a particular pH, the voltage difference between the active and reference electrodes for each such substrate 12 should be essentially equal. Such sensors are, therefore, interchangeable without any need for recalibration.

Thus in a device employing a pH blood gas $CO_2$ sensor made in accordance with the instant invention where a sensor has failed, a replacement made in accord with the instant invention may be installed without substantial need for recalibration.

The active 13 and reference 14 electrodes having been applied to substrate 12, and the dielectric insulating coating 18 having been applied to at least portions of the substrate and portions of the electrodes 13, 14, and the electrodes 13, 14 having been formed into junction type electrodes, optionally the substrate may include a membrane 20 applied over at least those portions of the substrate 12 and electrodes 13, 14 not coated with the insulated dielectric coating. Particularly where the sensor is to be used transcutaneously for sensing, for example, blood gas carbon dioxide levels, a membrane is particularly desirable. Any such membrane 20 should be one relatively tightly retaining electrolyte within any porous or chemical infrastructure of the membrane. Particularly, where a sensor incorporating such a membrane is to be utilized, for example, in transcutaneous blood gas sensing, the membrane should relatively tightly retain any electrolyte while in contact with the atmosphere. Yet, where any such sensor is to be used for the measurement of, for example, blood gas carbon dioxide levels, the membrane should be readily permeable by the carbon dioxide gas being sensed.

The membrane, preferably, is comprised of a polymeric or copolymeric material. By polymeric what is meant is a compound comprised of at least two monomer units joined together. By copolymeric what is meant is a mixed polymer that is the product of polymerizing two or more monomers and/or polymers at the same time. While the polymeric membrane can be applied to the substrate in any suitable or conventional manner, in this best embodiment the polymeric membrane material is dispersed, dispersion including at least partial solvation, in a suitable or conventional fluid to form a liquid into which the substrate 12 and thereby the electrodes 13, 14 carried upon the substrate 12, may be introduced for dip coating.

Typically the polymeric materials employed for membranes applied to sensors in accordance with the instant invention are the so-called hydrogels and/or hydrophilic polymers, which polymers may be copolymeric in nature. These hydrogels or hydrophilic polymers generally are possessed with a capability for incorporating water into a physical or chemical infrastructure of the polymer and retaining the water within the infrastructure. Where the water happens to include one or more solutes, as would an electrolyte, the solutes also become incorporated within the infrastructure of the polymer. Where the sensor is to be employed for transcutaneous blood gas sensing, the polymeric membrane material must be permeable to carbon dioxide.

Polymers employed in the practice of the instant invention as polymeric membrane materials need not be pure polymers. From time to time it is desirable that a polymer include a relatively insignificant quantity of an impurity that may be either: intrinsic to the production of the monomers prior to polymerization to form the polymer; or may be added to insure desirable characteristics in the polymer as employed for membrane purposes upon the substrate 12. Such impurities may induce a cross-linking effect within the polymer so as to forestall dissolution of the polymer while the sensor is in contact with an electrolyte.

Where a copolymer is employed to perform as a polymeric membrane, the co-polymers may be either regular copolymers containing substantially no contaminant material within any matrices of the polymer, or such copolymers may optionally include monomers such as N-vinyl pyrrolidone and glycidyl methacrylate and/or other additives such as plasticizers that may enhance desired characteristics of the copolymer such as carbon dioxide permeability.

Suitable or conventional polymeric materials and copolymeric materials polymerized from: hydroxyalkyl acrylates and hydroxyalkyl methacrylates such as hydroxyethyl acrylate, hydroxylpropyl acrylate, and hydroxybutyl methacrylate; epoxy acrylates and epoxy methacrylates, such as glycidyl methacrylate; amino alkyl acrylates and amino alkyl methacrylates; N-vinyl compounds, such as N-vinyl pyrrolidone, N-vinyl carbazole, N-vinyl acetamide, and N-vinyl succinimide; amino styrenes; polyvinyl alcohols and/or polyvinyl amines, necessarily made from suitable polymeric precursors; polyacrylamide and/or substituted polyacrylamides; vinyl pyrridine; vinyl sulfonate and polyvinyl sulfate; vinylene carbonate; vinyl acetic acid; vinyl crotonic acid; allyl amine; allyl alcohol; and vinyl glycidyl ethers find utility for use as membranes in the practice of the instant invention. Processes and procedures for creating such copolymers and/or homopolymers from the foregoing monomers are well-known and understood.

For pH sensors, the use of a cation permeable, and particularly hydrogen ion permeable membrane is desirable. While a variety of cationic exchange materials may be utilized, one material in particular has found acceptance as a result of broad resistance to chemical attack. Membranes fabricated from copolymeric vinyl ethers, products of E. I. duPont, called Nafion ® have produced superior results in electrochemical cells and particularly in chlorine cells.

Those NAFION compounds are known as perfluorocarbons and are a copolymer of at least two monomers with one monomer being selected from a group including vinyl fluoride, hexafluoropropylene, vinylidene fluoride, trifluoroethylene, chlorotrifluoroethylene, perfluoro(alkylvinyl ether), tetrafluoroethylene and mixtures thereof.

The second monomer often is selected from a group of monomers usually containing an $SO_2F$ or $COF$ group. Examples of such second monomers can be generally represented by the formula $CF_2=CFR_1SO_2F$ or $CF_2=CFR_1COF$. $R_1$ in the generic formula is a bifunctional perfluorinated radical comprising generally 1 to 8 carbon atoms but upon occasion as many as 25. One restraint upon the generic formula is a general requirement for the presence of at least one fluorine atom on the carbon atom adjacent the $-SO_2$ or $COF$ group, particularly where the functional group exists as the $-(-SO_2NH)_mQ$ form. In this form, Q can be hydrogen or an alkali or alkaline earth metal cation and m is the valence of Q. The $R_1$ generic formula portion can be of any suitable or conventional configuration, but it has been found preferably that the vinyl radical comonomer join the $R_1$ group through an ether linkage.

Typical sulfonyl or carbonyl fluoride containing monomers are set forth in U.S. Pat. Nos. 3,282,875; 3,041,317; 3,560,568; 3,718,627 and methods of preparation of intermediate perfluorocarbon copolymers are set forth in U.S. Pat. Nos. 3,041,317; 2,393,967; 2,559,752 and 2,593,583.

The particular nature of the polymeric membrane material employed is not critical provided that, where carbon dioxide is to be sensed, the polymeric membrane material be one permeable to carbon dioxide. Further, where the sensor is to be used for transcutaneous or invasive sensing of such representations of bodily functions as pH or carbon dioxide blood gas levels, the polymeric membrane material should be non-toxic, and one not readily soluble in bodily fluids.

After the membrane has been applied to the substrate and electrode portions of the sensor 10, the resulting finished sensor may be stored sans electrolyte and, before use, soaked in an appropriate electrolyte. Where the sensor is to be employed for pH and/or blood gas sensing functions, the electrolyte should be one which undergoes a suitable change in $H^+$ concentration with changes, for example where sensing carbon dioxide, in the atmospheric partial pressure of carbon dioxide reflected as a quantity of $CO_2$ gas dissolved in the electrolyte. In an equally preferred alternate, the sensor may be saturated with an electrolyte solution and stored in an electrolyte saturated state within a hermetically sealed container until the sensor is needed for use. Likewise, where the resulting finish sensor is to be used for pH and/or blood gas sensing of bodily functions, the electrolyte should be one that is non-toxic and one that, preferably, is non-irritating to the animal upon which it is applied.

It is also possible and in some cases advantageous to coat the whole finished sensor with the exception of the contact points with a material that is fluid impermeable, blood compatible and when used upon a $CO_2$ sensor, gas permeable. This would in effect create a system wherein the electrolyte would not contact the patient at all. Examples of such materials are, for example, polytetrafluoroethylene, polyphenylene oxide (PPO), polyethylene and polypropylene. It is also contemplated that in such a so-called sealed configuration the sensor of the present invention may be used as an invasive type sensor.

In one preferred embodiment of the present invention the electrolyte is a sodium bicarbonate solution, preferably in a range of from about 0.05 molar to 0.50 molar and most preferably about 0.15 molar. Such solutions, readily prepared, are nonirritating to skin areas such solutions may contact, and have a proven efficacy based upon use in the so-called Severinghaus electrode. Other suitable or conventional electrolytes may be employed. Optionally, any of these electrolytes may contain chloride ions. Examples of such other suitable electrolytes include, for example, 0.1 molar sodium bicarbonate or 0.1 molar potassium bicarbonate solution.

Referring to FIG. 1, each electrode 13, 14 includes an area 25 or zone whereby electrical contact may be made between the electrode and sensing instrumentation 50 shown best in FIG. 5. Typically, these connections 25 are electrically insulated and waterproofed by, for example, applying a silicone adhesive to the electrical contacts. Where, however, the sensor of the instant invention is intended for use as a transcutaneous carbon dioxide blood gas sensor, and where the electrical contacts 25 are applied to a surface of the substrate 12 obverse to the substrate surface having the electrodes 13, 14, then no such insulative waterproofing material may be necessary. Any suitable or conventional electrical device for comparing electrical output of the active electrode 13 against the reference electrode 14 may be employed in interpreting the output of the sensor of the instant invention.

The sensor 10 of the instant invention, employing a palladium/palladium oxide active electrode and a silver/silver chloride reference electrode, typically can produce electrochemical potentials ranging between −1.00 volts and +1.00 volts depending upon the pH of a particular electrolyte then in contact with the electrodes. Any electrical sensing device 50 employed in the practice of the instant invention must be capable of distinguishing within the voltage range (+1.00 to −1.0 V) between much smaller changes in voltage attributable to changes in pH of electrolytes in contact with the electrodes 13, 14.

Figure 2A:
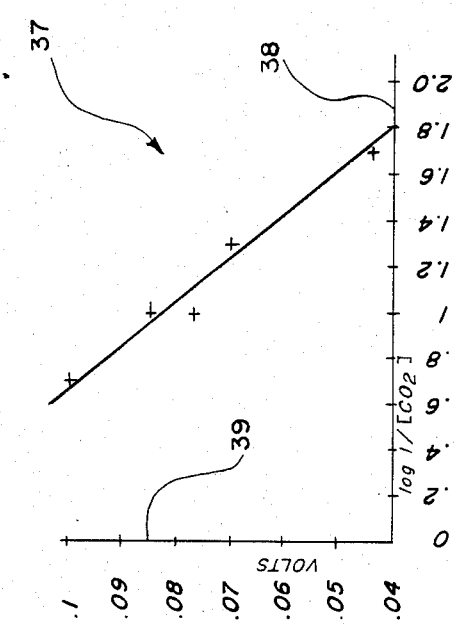
FIG. 2A is a graphical representation of the voltage output of a sensor made in accordance with the instant invention plotted against time for varying partial pressures of carbon dioxide in contact with the sensor.

Referring to the drawings, FIG. 2A displays a graphical representation 26 between time plotted in minutes along an abscissa 27 and voltage plotted along an axis 28 for varying concentrations of carbon dioxide contained in air being contacted with a sensor made in accordance with the instant invention having a palladium/palladium oxide active electrode and a silver/silver chloride reference electrode. The sensor was coated with a terpolymer of N-vinyl pyrrolidone/glycidyl methacrylate/HEMA. The graphical representation 26 includes a zone 29 wherein the concentration of carbon dioxide was 2 volume percent, a zone 30 wherein the $CO_2$ $CO_2$ concentration was 5 volume percent, a zone 31 wherein the concentration was 10 volume percent, and a zone 32 wherein the concentration of carbon dioxide was 20 volume percent. A zone 33 denotes the output voltage of the sensor where air containing ambient quantities of carbon dioxide contacted the sensor.

Figure 2B:
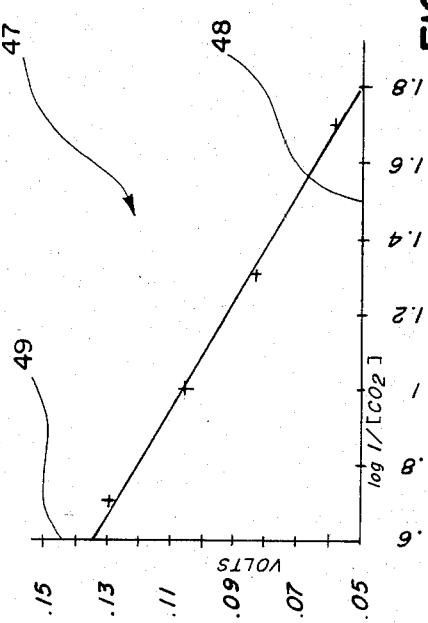
FIG. 2B is a graphical representation of a voltage output from a sensor made in accordance with the instant invention plotted against log $1/[CO_2]$.

FIG. 2B depicts a graphical representation 37 of a relationship between a log of $1/[CO_2]$ plotted along an abscissa 38 and voltage plotted along an axis 39. The relationship plotted in FIG. 2B was derived from the graphical representation of FIG. 2A.

Figure 3A:
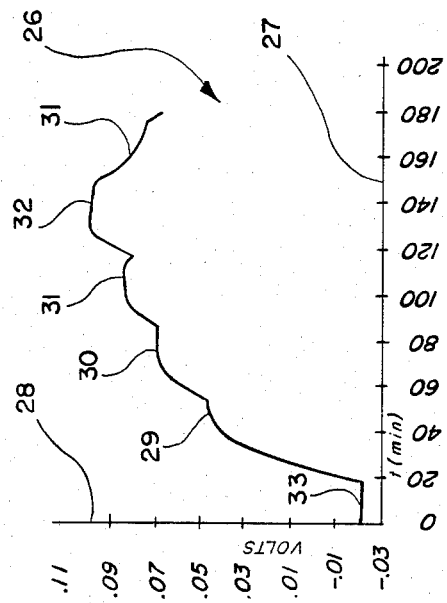
FIG. 3A is a graphical representation of a voltage output from a sensor made in accordance with the instant invention plotted against time for varying concentrations of carbon dioxide gas contacting the sensor.

Referring to the drawings, FIG. 3A defines a graphical representation 40 of a relationship between time plotted in minutes along an abscissa 41 and voltage plotted along an axis 42 for varying concentrations of carbon dioxide in air contacted with a sensor made in accordance with the instant invention and having a palladium/palladium oxide active electrode and a silver/silver chloride reference electrode. The sensor included a poly-HEMA membrane type coating applied to the sensor and electrodes. The graphical representation 40 includes a zone 43 wherein the carbon dioxide concentration of gas contacting the sensor was 2 percent by volume, a zone 44 wherein the carbon dioxide content of gas contacting the sensor was 5 percent by volume, a zone 45 wherein the carbon dioxide content of gas contacting the sensor was 10 percent by volume, and a zone 46 wherein the concentration of carbon dioxide in gas contacting the sensor was 20 percent by volume.

Figure 3B:
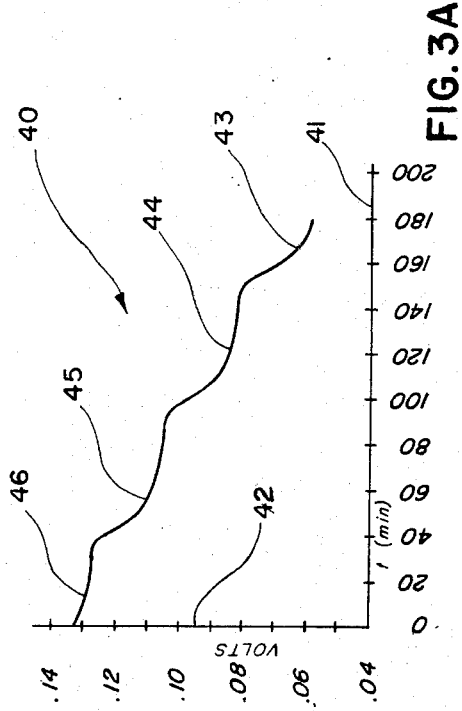
FIG. 3B is a graphical representation of a voltage output for a sensor made in accordance with the instant invention plotted against log $1/[CO_2]$ of carbon dioxide gas contacting the sensor.

FIG. 3B provides a graphical representation 47 of a relationship between log of 1 divided by the concentration of $pCO_2$ plotted along an abscissa 48 and voltage plotted against an axis 49 based upon the graphical representation 40 shown in FIG. 3A.

FIG. 5 is a schematic representation of an electrical instrument suitable for use in monitoring the voltage output of a sensor made in accordance with the instant invention.

Figure 5A:
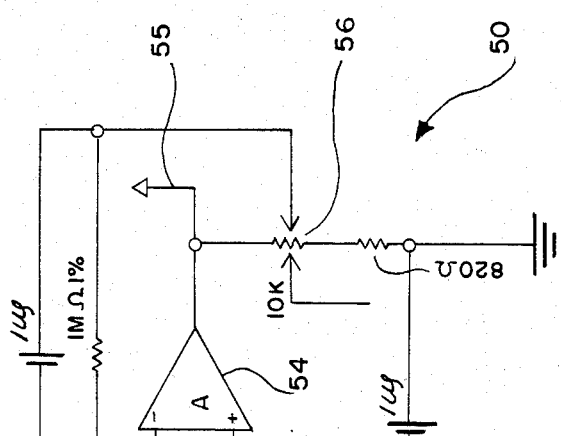
FIGS. 5A and 5B, is a schematic representation of an electrical interpretive device useful for measuring potential differences between electrodes utilized in the invention.

Referring to the drawings, FIG. 5A depicts an electrical schematic for an electrical instrument 50 suitable for measuring the electrical differences between the active electrode 13 and the reference electrode 14 as affixed upon the sensor 10 of the instant invention. The electrical instrument 50 includes operational amplifiers 51, 52 of any suitable or conventional nature. The operational amplifiers 51, 52 collect electrical signals (voltage) produced from the electrodes 13, 14 and provide a voltage following (amplification factor of 1) function for those electrical signals. The output of the operational amplifiers 51, 52 is presented to an operational amplifier 53 wherein the voltage signals are compared and their difference produced as an output. The output of the operational amplifier 53 is collected by an operational amplifier 54 producing a final voltage output signal 55. Potentiometers 56, 57 are provided for zeroing adjustment and calibration adjustment respectively in well known manner.

Figure 5B:
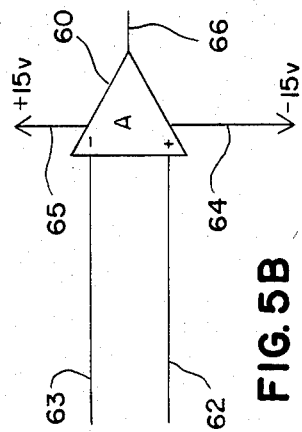

FIG. 5B depicts an operational amplifier suitable for use in the electrical instrument 50 shown in FIG. 5A. The operational amplifier 60 includes collection legs 62, 63 and power supply collection legs 64, 65 together with an output leg 66. Typically the operational amplifier is provided with +15 volts D.C. to the leg 65 and −15 volts D.C. to the leg 64. Such operational amplifiers are commercially available, and for example a suitable operational amplifier for use in the electrical instrument 50 is designated OP-7 and is available from Precision Monolithics Inc.

The following examples are provided to more fully illustrate the invention.

EXAMPLE 1

Three substrates measuring 0.85 centimeters by 2.54 centimeters by 0.0635 centimeters were prepared from an alumina material obtained from 3M Corporation (AlSiMag #614). A palladium metal electrode was applied by silk screening onto each substrate using a palladium ink obtained from Cermalloy (Catalog #C110/5043, Custom Formulation). The palladium electrodes were fired in accordance with instructions provided by Cermalloy. A silver electrode was then silk screened onto each of the substrates, parallel to and closely adjacent each palladium electrode, using a silver ink obtained from Electroscience Laboratories, Inc. (Catalog #9990). The silver electrode was then fired in accordance with standard firing instructions provided by Electroscience Laboratories. Each deposited electrode measured approximately 6 mm × 23 mm.

A ceramic dielectric coating obtained from Electroscience Laboratories, Inc. (Catalog #4612) was printed upon the surface of the substrate to which the electrodes had been applied using photo-resist and screening techniques such that only a small contact point with respect to the electrodes was exposed at one end of the substrate while an exposed area of each electrode measuring approximately 6 mm × 15 mm was left uncovered by the dielectric coating adjacent the opposite end of the substrate. The ceramic dielectric coating was applied in accordance with manufacturer's instructions. Each substrate was then immersed in a fused salt electrolyte at 335° C., the electrolyte including 99.0% (weight) $NaNO_3$ and 1.0% (weight) LiCl. The palladium metal electrode was made anodic within this fused salt electrolyte relative to a platinum counter electrode. Electrical current in a range of 5 to 20 milliamperes per square centimeter of palladium metal surface was conducted between the palladium metal electrode and the platinum counter electrode until a desired matte black appearance indicating the presence of palladium oxide was manifest upon the electrode. That is, the substrate was alternately cyclically made anodic and cathodic for 60 seconds each, for three cycles, then made anodic for 180 seconds and finally cathodic for 300 seconds. The substrates, now including a palladium/palladium oxide junction type electrode were removed from the melt and rinsed with deionized water.

The substrates were then immersed in a 1% aqueous sodium chloride solution adjacent a platinum screen. A potential of 3.5 volts was applied between the silver electrode, as an anode, and the platinum screen, as a cathode. Current flowing between the silver electrode and the platinum screen was adjusted to maintain approximately 5.6 milliamperes per square centimeter of silver electrode surface. After 40 seconds, the electrical polarization between the silver electrode and the platinum screen was reversed for 20 seconds and then reversed again, and maintained anodic for an additional period of ten minutes to produce a silver/silver chloride reference electrode. The substrates were then removed from the sodium chloride solution and washed with water.

A mixture of hydroxyethylmethacrylate (HEMA), glycidyl methacrylate (GMA), and N-vinyl-2-pyrrolidone in a mole ratio of 4:50:46 respectively was polymerized in a 75:25 mole ratio of methylethyl ketone and methanol. After polymerization, the polymerization mixture included 28% solids by weight. The sensors were then dipped in the polymerization mixture remaining in the polymerization mixture for approximately 3 seconds, to apply a polymer coating to those portions of the substrates not covered by the dielectric insulated coating. The sensors were then dried briefly in air at 60° C. and then at room temperature overnight and the dip coating and drying steps were repeated. Two 28 gauge (AWG) wires were soldered using a 60% tin electrical grade rosin solder one each to the palladium/palladium oxide electrode contact point and the silver/silver chloride electrode contact point and the entire area about each soldered contact point was covered with quick setting five minute epoxy cement obtained from DEV-CON ®. Each substrate was then immersed in a 0.15 molar solution of sodium bicarbonate for 48 hours.

A testing cell was provided having a total volume of 4.35 cubic centimeters and having provision within the cell for supporting two of the sensors mounted in opposition one to the other within the cell. Holes were provided upon the cell whereby wires communicating electrical information from the sensors were passed from the cell for interconnection with an electrical interpretative device. The sensors, conditioned in sodium bicarbonate, were placed within the cell and the wire passages through the cell were sealed in an air tight relationship with a silica type adhesive obtained from Dow Corning. The cell was provided with a gas inlet configured to flush the cell on a continuous basis with the desired gaseous mixture. The gas inlet included a bubbler type humidifier whereby gas entering the cell could be made to conform to a desired humidity. A flow meter was provided on the gas inlet to provide very constant desired gas flowrate throughout experimentation, the flowrate being independent of the pressure of the particular source of the gas. For purposes of this example, standardized compressed gas mixtures of carbon dioxide in nitrogen and carbon dioxide in compressed air were used.

Varying mixtures of carbon dioxide in air and nitrogen were introduced into the testing cell and the resultant voltage output of the sensors is displayed in FIG. 2A. In FIG. 2B, the voltage output of the sensors present in the testing cell is correlated with the log of the inverse of the partial pressure. A linear relationship obtains.

EXAMPLE 2

Three sensors were prepared in accordance with Example 1 except that these sensors were immersed for 3 seconds in a 10 percent by weight solution of poly-HEMA in methanol, and then were dried in a manner equivalent to Example 1. Immersion and drying was repeated once. The resulting sensors having a poly-HEMA coating were then provided with electrical contacting wires in accordance with Example 1 and were immersed in sodium bicarbonate in accordance with Example 1 for 120 hours. The sensors were then placed in the testing cell of Example 1 with the results being presented in FIGS. 3A and 3B. A linear relationship between voltage and the log of the inverse of the partial pressure of carbon dioxide present in the testing cell obtains.

EXAMPLE 3

Figure 4:
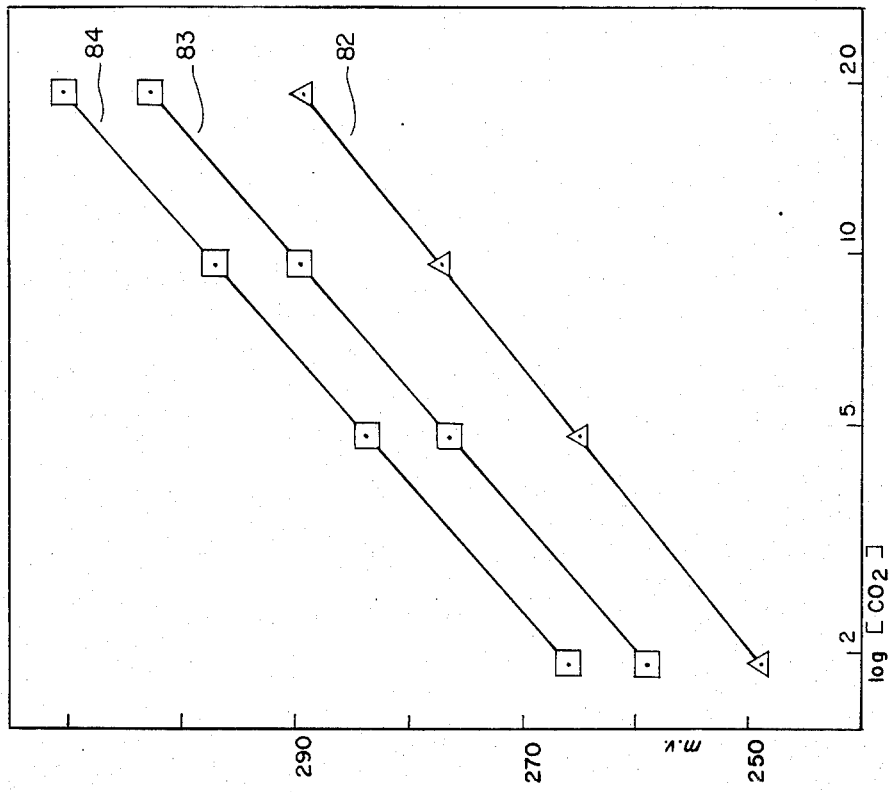
FIG. 4 is a graphical representation of a voltage produced by sensors made in accordance with the instant invention plotted against the log of the concentration of carbon dioxide in a gaseous substance contacting the sensor.

Example 2 was repeated except that the palladium/palladium oxide junction type electrode was applied by sputtering palladium onto the alumina substrate. A 6 percent by weight solution of poly-HEMA in methanol was spread over the electrode and substrate portions not covered by the insulative dielectric material and the methanol was allowed to evaporate at room temperature. The sensors were then immersed in a solution of 0.15 molar sodium bicarbonate in a 1:1 mole ratio of water and ethylene glycol. Two of the resulting sensors were inserted in the testing cell in accordance with Example 1 and subjected to contact with nitrogen containing varying quantities of carbon dioxide. Referring to the drawings, FIG. 4 depicts a graphical relationship between the percentage of carbon dioxide and nitrogen contacting these sensors plotted along an abscissa 80 and voltage plotted as millivolts along an axis 81. One plot 82 corresponds to millivolt of output of one of the two sensors mounted in the testing cell while carbon dioxide content of the nitrogen was being increased. A second plot 83 corresponds to millivolt output of the same sensor while carbon dioxide concentration contacting that sensor was being decreased. A third plot 84 corresponds to a millivolt relationship for the remaining sensor in the test cell as carbon dioxide content of the testing cell was being increased. It may be seen that the plots 82, 83, 84 are linear in relationship and have nearly identical slopes. Axis intercept differences between the plots 82, 84 are attributed to inaccuracy in the physical dimension of the electrodes applied by sputtering techniques to the substrates.

EXAMPLE 4

Substrates selected in accordance with Example 1 were subjected to thick film inking for applying electrodes in accordance with Example 1. Palladium/palladium oxide and silver/silver chloride junction electrodes were formed upon the substrates in accordance with Example 1. The resulting sensor assemblies were dipped into a 23.6 weight percent solution of poly- HEMA in methanol for approximately 3 seconds and then air dried at 60° C. for approximately 10 minutes. 28 gauge contact wires were soldered to the sensors for connection to electrical interpretative and data gathering equipment and any exposed metal around the electrical connections was sealed with Dow Corning silicon adhesive/sealant. The resulting sensors were then soaked in a pH 7.00 buffer for 66 hours.

These sensors were then placed consecutively into a number of phosphate buffers, the buffers varying in pH from 6.49 to 8.50. Potential differences between the palladium/palladium oxide electrode in the silver/silver chloride reference electrode were measured and are shown in FIG. 6.

Figure 6:
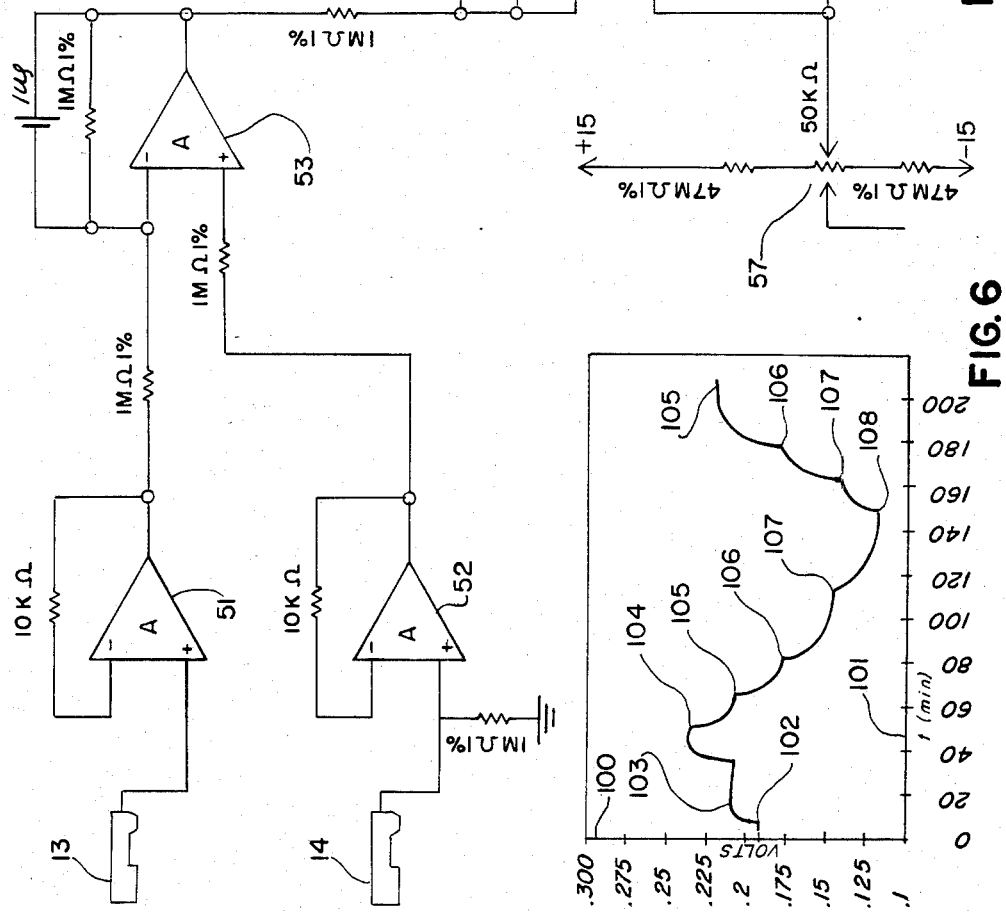
FIG. 6 is a graphical representation of voltage plotted against time for a particular pH sensor embodying the instant invention.

In FIG. 6 voltage is plotted along an axis 100 against time plotted along an abscissa 101. A pH of 7.2 is indicated by the reference numeral 102. Reference numeral 103 refers to a pH of 6.99. Reference 104 refers to a pH of 6.49. Reference numeral 105 refers to a pH of 6.99. Reference numeral 106 refers to a pH of 7.51. Reference numeral 107 refers to a pH of 7.99 and reference numeral 108 refers to a pH of 8.50.

While a preferred embodiment of the invention has been shown and described in detail, it will be apparent that various modifications and alterations may be made thereto without departing from the scope of the claims that follow.

What is claimed is:

1. A $CO_2$ gas sensor comprising:
    an electrically nonconductive substrate;
    a metal/metal oxide junction type active electrode including an active electrode metal, the active electrode metal being applied to the substrate by one of thick film and thin film techniques, and the active metal being then subjected to electro-oxidizing conditions for a period of time sufficient to oxidize a portion of the applied active electrode metal, the applied active electrode metal being made cathodic prior to discontinuance of the electro-oxidizing conditions;
    a silver/silver halide junction type reference electrode, adheringly applied to the substrate;
    an insulating, dielectric coating applied over at least portions of the substrate and electrodes;
    and a polymeric membrane comprising a laminate of a hydrophobic polymeric material atop a hydrophilic membrane material applied over at least those portions of the electrodes not having the insulating dielectric coating applied thereto, the polymeric membrane being capable of relatively rapidly transmitting $CO_2$ thereacross, and the polymeric material including a liquid electrolyte bound by the polymeric membrane.

2. A method for making a solid state pH sensor comprising the steps of:
    selecting an electrically nonconducting substrate formed from a material selected from a group consisting essentially of ceramics, refractories, thermoplastics, and thermosetting resins;
    applying an active electrode metal to the substrate by one of thick and thin film techniques to form an electrode of desired physical configuration adhered to the substrate;
    adheringly applying to the substrate a silver/silver halide junction type reference electrode;
    oxidizing a portion of the active electrode metal by subjecting the active electrode metal to electro-oxidizing conditions for a period of time necessary to form a desired quantity of an oxide of the metal, the active electrode metal being made cathodic at least immediately prior to terminating the electro-oxidizing conditions; and
    applying to at least portions of the electrodes and the substrate an insulating dielectric coating.

3. The method of claim 2, the active electrode metal being applied by thick film screen printing of a precursor compound including the metal onto the substrate and then sintering the applied precursor to provide an active electrode metal upon the substrate.

4. The method of claim 3, the substrate being alumina, wherein electro-oxidation is accomplished by making the active electrode metal anodic within a fused salt electrolyte consisting of $NaNO_3$ and $LiCl$ salts under an impressed current of between about 0.1 milliamperes and 20.0 milliamperes per square centimeter of active electrode metal surface, followed by making the active electrode metal cathodic prior to removing the now active electrode from the fused salt electrolyte and including the step of: applying to at least those portions of the electrode not having an applied coating of an insulating dielectric a polymeric membrane capable of binding a liquid electrolyte within the polymeric membrane.

5. The method of claim 2, the substrate being alumina, wherein electro-oxidation is accomplished by making the active electrode metal anodic within a fused salt electrolyte consisting of $NaNO_3$ and $LiCl$ salts under an impressed current of between about 0.1 milliamperes and 20.0 milliamperes per square centimeter of active electrode metal surface, followed by making the active electrode metal cathodic prior to removing the now active electrode from the fused salt electrolyte and including the step of: applying to at least those portions of the electrode not having an applied coating of an insulating dielectric a polymeric membrane capable of binding a liquid electrolyte within the polymeric membrane.

6. A pH sensor produced by the method set forth in claim 3.

7. A method for making a $CO_2$ gas sensor comprising the steps:
    selecting an electrically nonconducting substrate formed from a material selected from a group consisting essentially of ceramics, refractories, thermoplastics, and thermosetting resins;
    applying an active electrode metal to the substrate by one of thick and thin film techniques to form an electrode of desired physical configuration adhered to the substrate;
    adheringly applying to the substrate a silver/silver halide junction type reference electrode;
    applying to at least portions of the electrodes and the substrate an insulating dielectric coating;
    oxidizing a portion of the active electrode metal by subjecting the active electrode metal to electro-oxidizing conditions for a period of time necessary to form a desired quantity of an oxide of the active electrode metal, the active electrode metal being made cathodic prior to terminating the electro-oxidizing conditions; and
    applying to at least those portions of the resulting sensor not having an applied coating of an insulating dielectric a polymeric membrane comprising a laminate of a hydrophobic polymeric material atop a hydrophilic membrane material capable of binding a liquid electrolyte within the polymeric membrane, electro-oxidation being accomplished by making the active electrode metal anodic within a fused salt electrolyte consisting of NaNO₃ and LiCl salts under an impressed current of between about 0.1 milliamperes and 20.0 milliamperes per square centimeter of active electrode metal surface, followed by making the now active electrode cathodic prior to removing the active electrode from the fused salt electrolyte.

8. A method for making a transcutaneous blood $CO_2$ gas sensor comprising the steps:
selecting an electrically nonconducting substrate formed from alumina;
applying an active electrode metal to the substrate by one of thick and thin film techniques to form an electrode of desired physical configuration adhered to the substrate;
adheringly applying to the substrate a silver/silver halide junction type reference electrode;
applying to at least portions of the electrodes and the substrate an insulating dielectric coating;
oxidizing a portion of the active electrode metal by subjecting the active electrode metal to electro-oxidizing conditions for a period of time necessary to form a desired quantity of an oxide of the active electrode metal, the active electrode metal being made cathodic prior to terminating the electro-oxidizing conditions; and
applying to at least those portions of the resulting sensor not having an applied coating of an insulating dielectric a polymeric membrane comprising a laminate of a hydrophobic polymer material atop a hydrophilic membrane material capable of binding a liquid electrolyte within the polymeric membrane, and wherein electro-oxidation is accomplished by making the active electrode anodic within a fused salt electrolyte consisting of NaNO₃ and LiCl salts under an impressed current of between about 0.1 milliamperes and 20.0 milliamperes per square centimeter of active electrode metal surface, followed by making the now active electrode cathodic prior to removing the active electrode from the fused salt electrolyte.

9. The method of claim 8, the active electrode metal being applied by thick film screen printing of a precursor compound including the metal onto the substrate and then sintering the applied precursor to provide an active electrode metal upon the substrate.

10. A method for making a precious metal/precious metal oxide junction type electrode comprising the steps of:
selecting a precious metal electrode precursor the metal being selected from a group consisting of palladium, iridium, rhodium, ruthenium and osmium;
immersing at least a portion of the electrical precursor in a molten salt electrolyte;
making the electrode precursor anodic at an electrical current not exceeding about 20 milliamperes per square centimeter of immersed electrode precursor to form a desired quantity of the precious metal oxide; and
at least once making the electrode precursor cathodic prior to removal from the molten salt electrolyte at an electrical current not exceeding the current density while anodic.

11. A solid state pH sensor comprising:
an electrically nonconductive substrate;
a metal/metal oxide junction type active electrode including an active electrode metal, the active electrode metal being applied to the substrate by one of thick film and thin film techniques, and the active metal being then subjected to electro-oxidizing conditions for a period of time sufficient to oxidize a portion of the applied active electrode, the applied active electrode metal being made cathodic prior to discontinuance of the electro-oxidizing conditions;
a metal/metal halide junction type reference electrode, adheringly applied to the substrate; and
an insulating, dielectric coating applied over at least portions of the substrate and electrodes.

12. The sensor of claim 11 including a polymeric membrane capable of supporting hydrogen ion transport thereacross applied over at least those portions of the electrodes not having the insulating dielectric coating applied thereto.

13. The sensor of claim 11 wherein the metal/metal oxide electrode is palladium/palladium oxide and the metal/metal halide electrode is silver/silver halide.

* * * * *